United States Patent
Jones et al.

(10) Patent No.: US 7,409,077 B2
(45) Date of Patent: Aug. 5, 2008

(54) NEAREST-NEIGHBOR REBINNING IN CLINICAL PET USING ON-LINE THREE DIMENSIONAL LOR-TO-BIN MAPPING

(75) Inventors: William F. Jones, Knoxville, TN (US); John E. Breeding, Knoxville, TN (US); Bryan Castleberry, Knoxville, TN (US); Johnny Reed, Knoxville, TN (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 444 days.

(21) Appl. No.: 11/130,632

(22) Filed: May 16, 2005

(65) Prior Publication Data
US 2005/0253075 A1  Nov. 17, 2005

Related U.S. Application Data

(60) Provisional application No. 60/571,275, filed on May 14, 2004.

(51) Int. Cl.
*G06K 9/00* (2006.01)
(52) U.S. Cl. .................................. 382/128
(58) Field of Classification Search ............. 382/128, 382/131; 365/185.28, 118
See application file for complete search history.

(56) References Cited

U.S. PATENT DOCUMENTS

| | | | | |
|---|---|---|---|---|
| 5,347,384 A * | 9/1994 | McReynolds et al. | ......... | 398/58 |
| 6,785,165 B2 * | 8/2004 | Kawahara et al. | ...... | 365/185.28 |
| 6,947,585 B1 * | 9/2005 | Jones | ......................... | 382/131 |

OTHER PUBLICATIONS

K. Wienhard et al., "The ECAT HRRT: Performance and First Clinical Application of the New High Resolution Research Tomograph," IEEE Trans. Nucl. Sci., Feb. 2002, pp. 104-110, vol. 49.
W. Jones et al., "LSO PET/SPECT Spatial Resolution: Critical On-line DOI Rebinning Methods and Results," IEEE MIC Conf. Rec., Oct. 2000.
W. Jones et al., "First Time Measurement of Transaxial Resolution for a New High-Sensitivity PET Prototype Using 5 LSO Panel Detectors," IEEE MIC Conf. Rec., Nov. 2002.
P. R. G. Virador et al., "3-D Reconstruction in PET Cameras with Irregular Sampling and Depth of Interaction," IEEE Trans. Nucl. Sci., Aug. 2001, pp. 1524-1529, vol. 48, No. 4.

* cited by examiner

*Primary Examiner*—Tom Y Lu
(74) *Attorney, Agent, or Firm*—Peter L. Kendall

(57) ABSTRACT

A projection data rebinning device for nearest-neighbor rebinning in Positron Emission Tomography (PET) using on-line 3D axial LOR-to-bin mapping. The PETLINK™ DMA Rebinner (PDR) of the present invention includes a PCI card for on-line translation of detector-pair event packets into bin-address packets. The PDR delivers accurate axial and transaxial LOR nearest-neighbor rebinning and enables the more oblique LOR to be mapped into the proper sinogram bins. The PDR is used in association with hardware architecture in electrical communication with a medical imaging device. The data acquisition architecture includes a processor, random access memory (RAM), an operating system, and a data storage device. The PDR includes a plurality of FPGAs and flash chips. The FPGAs are in communication with each other via a high-bandwidth connection. The flash memory chips are used for look-up tables. The PDR performs on-line translation of detector-pair event packets into bin-address packets.

8 Claims, 3 Drawing Sheets

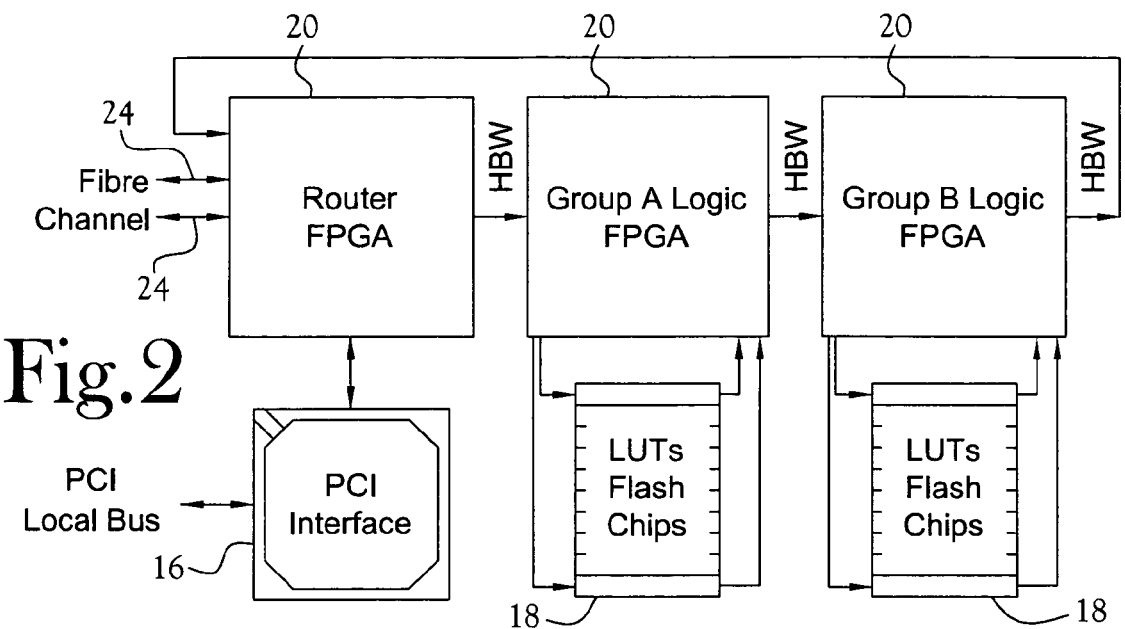
Fig.2
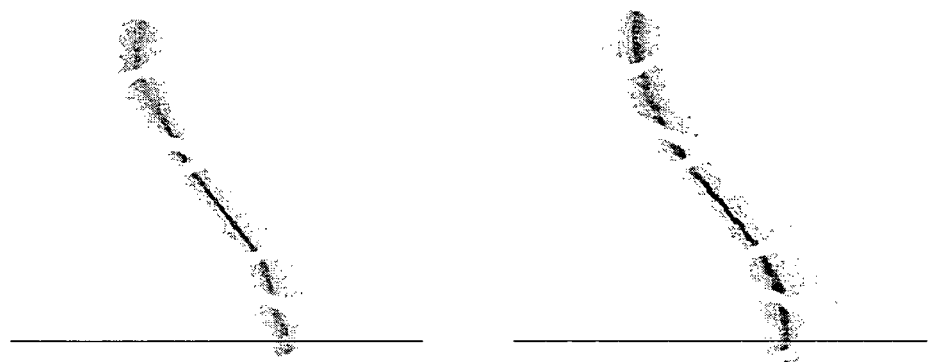
Fig.4A
(Prior Art)
Fig.5A
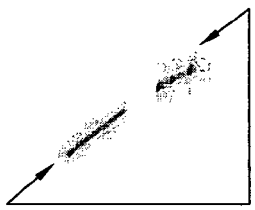
Fig.4B
(Prior Art)
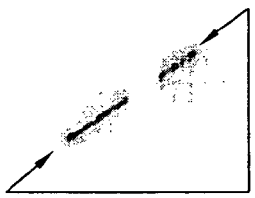
Fig.5B

NEAREST-NEIGHBOR REBINNING IN CLINICAL PET USING ON-LINE THREE DIMENSIONAL LOR-TO-BIN MAPPING

CROSS-REFERENCE TO RELATED APPLICATIONS

This application claims the benefit of U.S. Provisional Application No. 60/571,275, filed May 14, 2004.

STATEMENT REGARDING FEDERALLY SPONSORED RESEARCH OR DEVELOPMENT

Not Applicable

BACKGROUND OF THE INVENTION

1. Field of Invention

The present invention pertains to the field of Positron Emission Tomography (PET). More particularly, this invention is directed to a device for improving the speed and accuracy of on-line three-dimensional (3D) LOR-to-bin mapping.

2. Description of the Related Art

Various techniques are used for medical imaging. Positron emission tomography (PET) is one of several popular methods in radiology because of its ability to non-invasively study physiological processes and structures within the body. PET is a nuclear imaging technique used in the medical field to assist in the diagnosis of diseases. PET allows the physician to examine the whole patient at once by producing pictures of many functions of the human body unobtainable by other imaging techniques. In this regard, PET displays images of how the body works (physiology or function) instead of simply how it looks. PET is considered the most sensitive, and exhibits the greatest quantification accuracy, of any nuclear medicine imaging instrument available at the present time. Applications requiring this sensitivity and accuracy include those in the fields of oncology, cardiology, and neurology.

In PET, short-lived positron-emitting isotopes, referred to as radiopharmaceuticals, are injected into a patient. When these radioactive drugs are administered to a patient, they distribute within the body according to the physiologic pathways associated with their stable counterparts. As the radiopharmaceutical isotopes decay in the body, they discharge positively charged particles called positrons. Upon discharge, the positrons encounter electrons, and both are annihilated. As a result of each annihilation event, gamma rays are generated in the form of a pair of diametrically opposed photons approximately 180 degrees (angular) apart. After the PET scanner detects these annihilation "event pairs" over a period of time, the isotope distribution in a cross section of the body is reconstructed. These events are mapped within the patient's body, thus allowing for the quantitative measurement of metabolic, biochemical, and functional activity in living tissue. More specifically, PET images (often in conjunction with an assumed physiologic model) are used to evaluate a variety of physiologic parameters such as glucose metabolic rate, cerebral blood flow, tissue viability, oxygen metabolism, and in vivo brain neuron activity.

In PET, it is well know that data acquisition is limited by several physical constraints of the hardware implemented. A fundamental requirement for 3-D PET is the proper positioning of each coincidence event into the 3-D projection data space. Rebinning is a positioning calculation which may use a nearest-neighbor LOR-to-projection-bin mapping. When rebinning is performed rapidly, higher patient throughput results. High-sensitivity, high-resolution PET requires that more complex rebinning calculations be performed at higher rates. These requirements place increasing demands on the data acquisition electronics.

The pursuit of greater sensitivity in 3-D PET typically leads to ever-larger detector arrays and higher count rates. Preserving good image resolution in larger detector arrays requires more complex calculations. In the present case, more calculations are required for properly positioning coincidence LORs into the 3-D projection data space. As a result of this progression, algorithms and electronic architectures which were once adequate for the smaller, shorter-axis detector arrays are no longer adequate. As the axial extent of the detector array increases, the data acquired from conventional algorithms degrades. Accordingly, algorithms and electronic architectures required to service on-line rebinning for larger, longer-axis PET detector arrays must be improved, especially where image resolution is critical. One example of a long-axis high-resolution PET is described by Wienhard et al., "The ECAT HRRT: Performance and First Clinical Application of the New High Resolution Research Tomograph," *IEEE Trans. Nucl. Sci.*, vol. 49, pp. 104-110 (2002). With an eye toward the clinical needs of high patient throughput, challenges to the on-line electronics include more complex rebinning algorithms and higher rebinning rates.

In earlier work on digital pipelines for on-line PET rebinning, flash memory chips used as look-up tables (LUT) were applied in various pipeline stages using programmable logic. See, for example, W. Jones, et al., "LSO PET/SPECT Spatial Resolution: Critical On-line DOI Rebinning Methods and Results," *IEEE MIC Conf. Rec.*, (2000); and W. Jones, et al., "First Time Measurement of Transaxial Resolution for a New High-Sensitivity PET Prototype Using 5 LSO Panel Detectors," *IEEE MIC Conf. Rec.*, (2002).

BRIEF SUMMARY OF THE INVENTION

A projection data rebinning device for nearest-neighbor rebinning in Positron Emission Tomography (PET) using on-line 3D axial LOR-to-bin mapping is provided. The PETLINK™ Direct Memory Access (DMA) Rebinner (PDR) of the present invention is a PCI card for on-line translation of detector-pair event packets into bin-address packets. The device of the present invention receives and transmits event packets on dual Fibre Channel fiber-optic links as well as a 64/66 PCI interface. The present invention includes flash memory and an array of large capacity field programmable gate array (FPGAs) which, in combination, results in extreme flexibility for complex PET applications. The present invention delivers accurate axial and transaxial LOR nearest-neighbor rebinning and enables the more oblique LOR to be mapped into the proper sinogram bins, which is significant for optimal image resolution.

The PDR of the present invention is used in association with a hardware architecture that is in electrical communication with a medical imaging device. The data acquisition architecture includes a processor, random access memory (RAM), an operating system, and a data storage device.

The PDR includes dual full-duplex Fibre Channel fiber-optic transceivers capable of transmitting data at a minimum of 1 to 2 Gbps. In one embodiment, the PDR includes three primary FPGAs and 20 flash chips. This PC-format PCI card provides on-line rebinning for multiple PET detector configurations. The FPGAs are in communication with each other via a high-bandwidth (HBW) connection, with each HBW supporting 3.8 Gbps transfers of packet data. The dual Fibre Channel port supports either 1 or 2 Gbps. The 20 flash memory chips are used for look-up tables (LUTs).

The on-line translation in one embodiment of the present invention converts 64-bit detector-pair event packets into either 32-bit or 64-bit bin-address packets. In one embodiment, this translation is performed at rates approaching 15 M packets/sec. The pipeline delivers nearest-neighbor rebinning calculations at rates approaching 15 M event-packets/sec. The flash memory chips have a 4M×16-bit capacity and 60 ns access time.

The bin-address packets are stored in list-mode fashion to the data storage device or applied by PC application software for on-line histogramming into the PC-motherboard-resident DRAM. Alternatively, the PDR passes arriving 64-bit detector-pair packets in an unaltered state for list-mode storage to the data storage unit. In addition, previously stored 64-bit detector-pair packets are replayed through the PDR via a PCI bus to rapidly rebin into bin-address packets as a post-acquisition process. The PDR may also retransmit either unaltered or rebinned packets on its second FC port.

The PDR delivers on-line LOR nearest-neighbor rebinning for full 3-D PET, both axial and transaxial, at rates approaching 15 M events/sec. Seven pipeline stages are provided in the illustrated embodiment. It will be understood by those skilled in the art, however, that more or fewer stages may be provided within the scope of the present invention. Each of the stages is in communication with the next sequential stage via a digital FPGA latch of at least 64-bit capacity. 64-bit detector-pair packets are input to Stage 1 of the pipeline from a Router FPGA. Stage 1 provides encoding for both emission depth of interaction and transmission operation. Stage 2 generates a transaxial sinogram index and two axial correction parameters from the transaxial detector pair indexes. Stage 3 generates an uncorrected plane and segment, i.e., axial angle, indexes with an encoded ring difference value from the axial detector-pair indexes. Stage 4 generates a delta correction for both the plane and segment. Stage 5 generates corrected-for-true-axial-position plane and segment indexes. Stage 6 calculates a sinogram number as an index into the 3-D array of sinograms. Stage 7 calculates the final bin address value using FPGA-resident integer multipliers and adders. 64-bit bin-address packets are then output to the Router FPGA.

BRIEF DESCRIPTION OF THE SEVERAL VIEWS OF THE DRAWINGS

The above-mentioned features of the invention will become more clearly understood from the following detailed description of the invention read together with the drawings in which:

FIG. 2 is a block diagram showing one embodiment of a chip architecture incorporating various features of the PDR of the present invention;

FIGS. 4A and 4B illustrate projection space histograms from oblique LOR using a PRIOR ART rebinning algorithm; and FIGS. 5A and 5B illustrate projection space histograms from the same oblique LOR used to acquire the histograms of FIGS. 4A and 4B, the histograms of FIGS. 5A and 5B having been derived using a rebinning algorithm 100% compatible with the hardware architecture of the PDR of the present invention.

DETAILED DESCRIPTION OF THE INVENTION

A projection data rebinning device for nearest-neighbor rebinning in Positron Emission Tomography (PET) using on-line 3D axial LOR-to-bin mapping is provided. The PETLINK™ Direct Memory Access (DMA) Rebinner (PDR) of the present invention is illustrated generally at 10 in the figures. The PDR 10 includes a peripheral component interconnect (PCI) card 12 for on-line translation of detector-pair event packets into bin-address packets. The device of the present invention receives and transmits event packets on dual Fibre Channel fiber-optic links 14 as well as a 64/66 PCI interface 16. The present invention includes flash memory 18 and an array of large capacity field programmable gate array (FPGAs) 20 which, in combination, results in extreme flexibility for complex PET applications. The present invention delivers accurate axial and transaxial LOR nearest-neighbor rebinning and enables the more oblique LOR to be mapped into the proper sinogram bins, which is significant for optimal image resolution.

Figure 1:
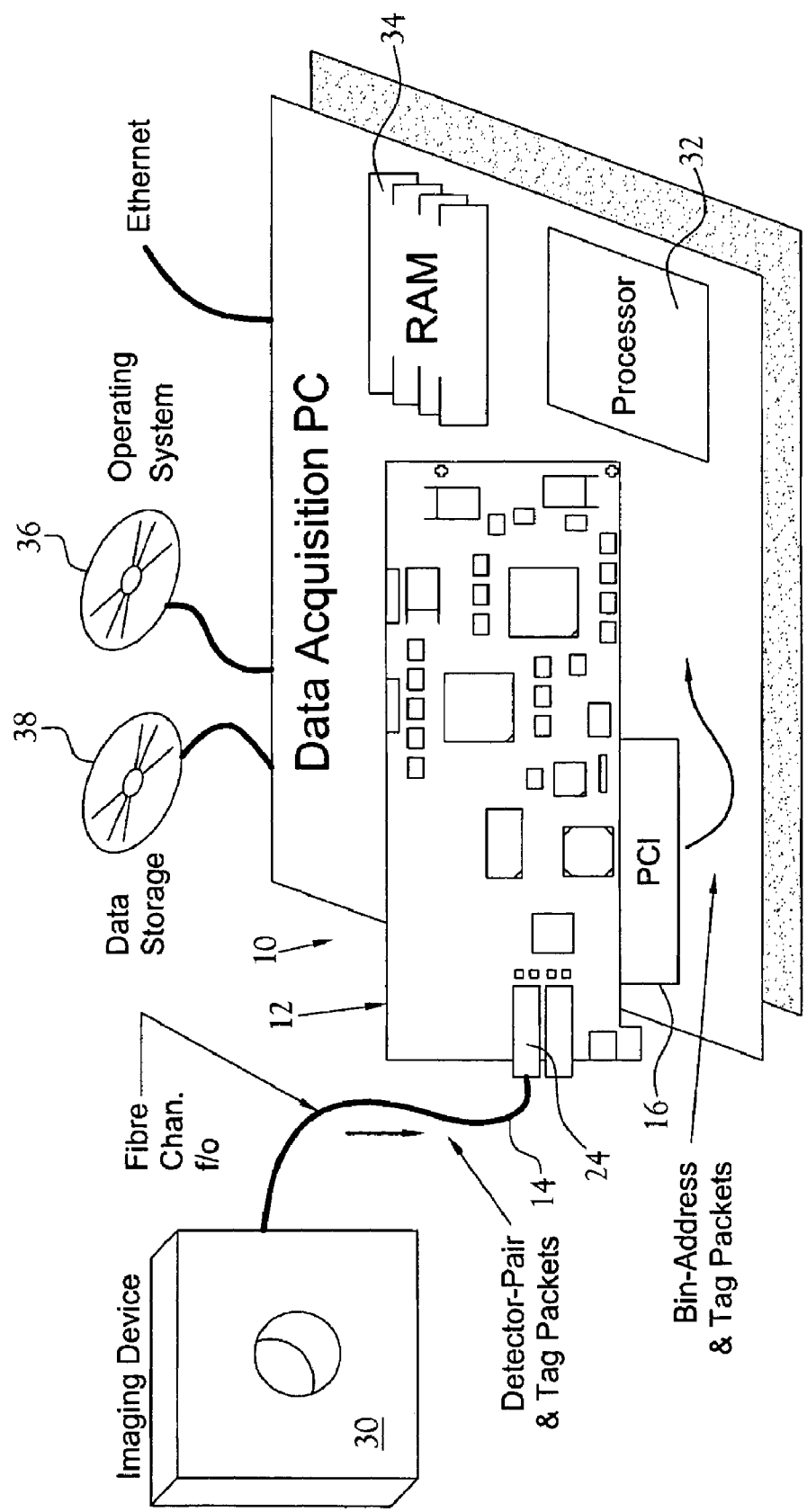
FIG. 1 a diagram of a PC-based data acquisition architecture incorporating the PETLINK™ DMA Rebinner (PDR) of the present invention.

FIG. 1 is a diagram of a PC-based data acquisition architecture incorporating the PDR 10 of the present invention. A medical imaging device 30 is in communication with the architecture. This communication is established in a conventional manner, such as, but not limited to electrically or via fiber optics. In the illustrated embodiment, the imaging device 30 is in fiber optic communication directly with the PDR 10. It will be understood that other connection arrangements are within the scope of the present invention. Also illustrated in association with the data acquisition architecture are a processor 32, random access memory (RAM) 34, an operating system 36, and a data storage device 38.

The PDR 10 is more clearly illustrated in FIG. 2, which is a block diagram showing the chip architecture of the device 10 of the present invention. The transceivers 24 of the preferred embodiment are capable of transmitting data at a minimum of 1 to 2 Gbps. Illustrated are three primary FPGAs 20 and 20 flash chips 18. However, it will be understood that more or fewer of each may be provided within the scope of the present invention. In the preferred embodiment, the flash chips 18 are capable of 4M×16-bit, at 60 ns access times. This PC-format PCI card 12 provides on-line rebinning for multiple PET detector configurations. A 64/66 PCI interface is shown. Each of 3 high-bandwidth (HBW) connections from FPGA to FPGA support 3.8 Gbps transfers of packet data. The dual Fibre Channel (FC) port 24 supports either 1 or 2 Gbps. The 20 flash memory chips 18 are used for look-up tables (LUTs).

Extreme flexibility in this architecture comes from general-purpose flash-to-FPGA connections which are not specific to any one pipeline application. For the PDR 10, the pipeline is more flexibly formed within the FPGA 20 and less dependent upon fixed PCB connections. Individual flash memory chips 18 are not locked into serving only one, arbitrary pipeline stage and are instead much more effectively grouped according to the application.

While it will be understood that other configurations are within the scope of the present invention, the on-line translation in one embodiment of the present invention converts 64-bit detector-pair event packets into either 32-bit or 64-bit bin-address packets. In one embodiment, this translation is performed at rates approaching 15 M packets/sec. The pipeline delivers nearest-neighbor rebinning calculations at rates approaching 15 M event-packets/sec. The flash memory 18 in the illustrated embodiment includes a set of 20 chips, each with 4M×16-bit capacity and 60 ns access time. Further, in the illustrated embodiment, three FPGAs 20 are included, each with greater than 600 user input/output (I/O) pins.

The bin-address packets are stored in list-mode fashion to the data storage device 38 or applied by PC application software for on-line histogramming into the PC-motherboard-resident RAM 34. Alternatively, the PDR 10 passes arriving 64-bit detector-pair packets in an unaltered state for list-mode storage to the data storage device 38. In addition, previously stored 64-bit detector-pair packets are replayed through the PDR 10 via a PCI bus 16 to rapidly rebin into bin-address packets as a post-acquisition process. The PDR 10 may also retransmit either unaltered or rebinned packets on its second FC port 24.

Figure 3:
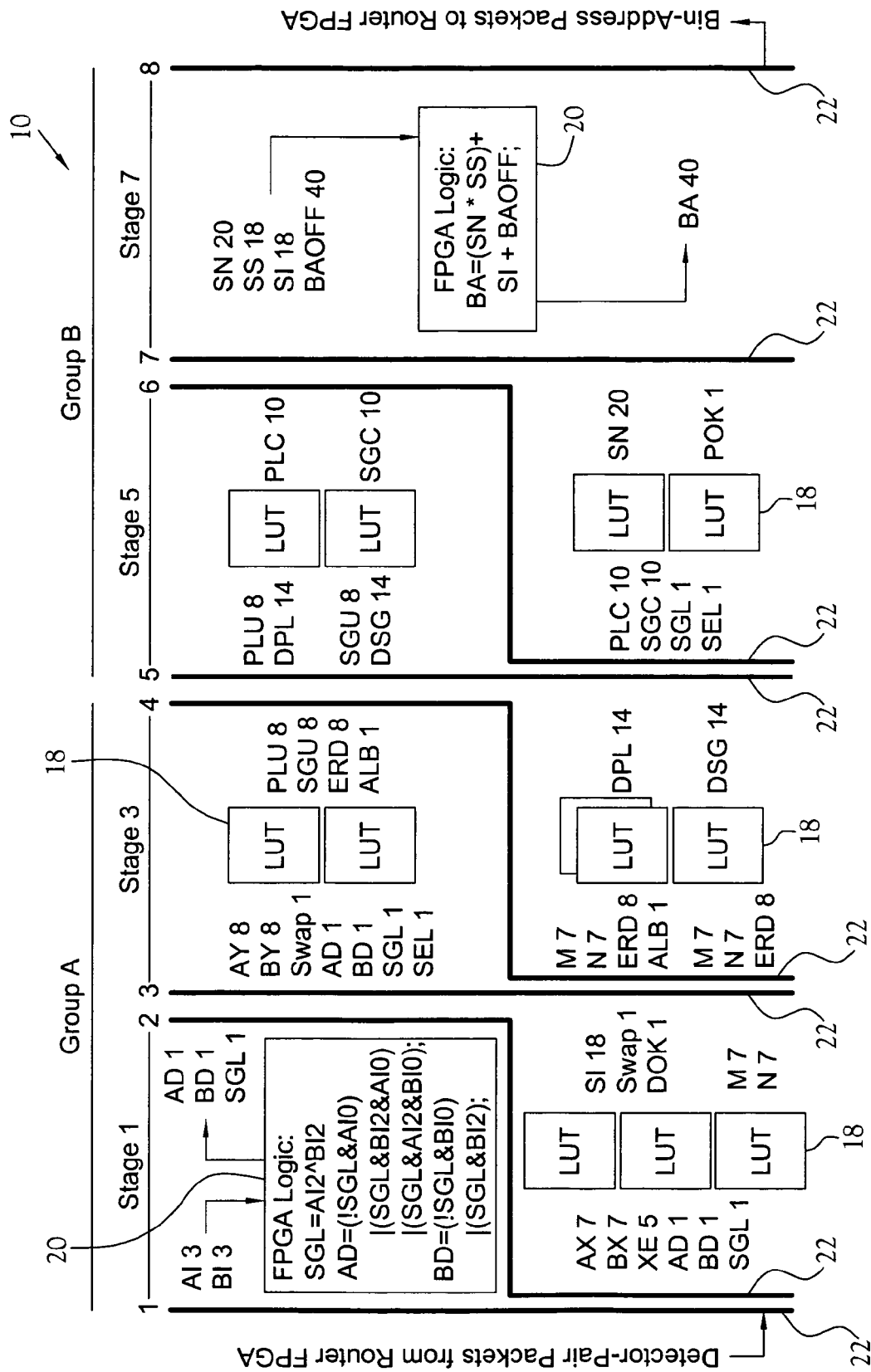
FIG. 3 is a diagram of one embodiment of a PDR digital pipeline incorporating various features of the PDR of the present invention.

FIG. 3 is a diagram of one embodiment of the PDR digital pipeline of the present invention. The illustrated embodiment of the PDR 10 delivers on-line LOR nearest-neighbor rebinning for full 3-D PET, both axial and transaxial, at rates approaching 15 M events/sec. Seven pipeline stages are shown. Each LUT block represents a distinct 4M×16-bit flash memory chip. It will be understood by those skilled in the art that other pipeline configurations are possible with this general-purpose PDR architecture. In the illustrated embodiment, a 7-stage digital pipeline is provided flowing from left to right. Each of the stages is in communication with the next sequential stage via a digital FPGA latch 22 of at least 64-bit capacity. At diagram left, 64-bit detector-pair packets are input to the pipeline from the Router FPGA (not shown). Each LUT block represents a 4M×16-bit flash memory chip with input parameter labels on the left, representing addresses, and output labels on the right, representing data. Stage 1 provides encoding for both emission depth of interaction and transmission operation. Here AD1 and BD1 are single-bit depth indexes. Stage 2 generates an 18-bit transaxial sinogram index SI18 and two 7-bit axial correction parameters M7, N7 from the transaxial detector pair indexes AX, BX, XE, etc. The SEL bit asserts one of two LUT functions as needed, for example, Span 3/Span 9. The Swap bit corrects the AxB/BxA sinogram boundaries. The DOK bit is true for LOR within the specified FOV diameter.

Stage 3 generates 8-bit uncorrected plane PLU8 and segment, i.e., axial angle, indexes SGU8 with an encoded ring difference ERD8 value from the axial detector-pair indexes AY, BY, etc. The ALB bit indicates AY less than BY. Stage 4 generates a 14-bit delta correction for both the plane DPL14 and segment DSG14. Stage 5 generates corrected-for-true-axial-position plane PLC10 and segment SGC10 indexes. Stage 6 calculates the 20-bit sinogram number SN20 as an index into the 3-D array of sinograms. The POK bit is true for LOR not exceeding an oblique angle limit. Stage 7 calculates the final 40-bit bin-address value BA40 using FPGA-resident integer multipliers and adders. A "sinogram-size" constant SS18 is set to 73,728 (=256×288) for the HRRT. A general purpose FPGA-register-driven bin-address-offset value BAOFF40 is supported. At diagram right, 64-bit bin-address packets are output to the Router FPGA.

The illustrated implementation of the PDR 10 is provided for emission operation of the imaging device 30. While specific values for the variables are discussed, i.e., number of bits, it will be understood by those skilled in the art that other values may be implemented as well while remaining within the spirit of the present invention, and such values are exemplary only.

Illustrated in FIGS. 4A and 4B and FIGS. 5A and 5B, respectively, is a comparison of images acquired using a needle source disposed within the field of view (FOV) of an imaging device 30. Because the needle is linear, the resulting two-dimensional image (FIGS. 4B and 5B) should likewise be linear. A 3 hour acquisition was performed collecting approximately 800 M 64-bit detector-pair packets into a list-mode file. These figures illustrate projection data from the acquisition. More specifically, the projection data in each figure is from far oblique LOR—i.e. segment +22 of 45. Illustrated in FIGS. 4A and 4B, a prior art hardware-emulating rebinning algorithm was used. This prior art rebinning algorithm does not have sufficient means to properly map the far oblique LOR into the 3-D projection space, as illustrated by the poor sine-wave trajectory illustrated in FIG. 4A and the non-linear 2-D view illustrated in FIG. 4B. To this extent, FIG. 4A illustrates a transaxial sinogram and FIG. 4B illustrates a 2-D view extracted from the 3-D projection space.

FIGS. 5A and 5B illustrate similar projections to those of FIGS. 4A and 4B, respectively, using a rebinning algorithm 100% compatible with the hardware architecture of the device of the present invention. It is illustrated by the better results that the present invention provides the capacity to accurately position the far oblique LOR into the 3-D projection space. With respect to FIG. 5A, it is noted that the sine-wave trajectory is much more correct. Attention is drawn both to the clarity of the line, as well as the better defined curve at the lower right. In contrasting the curve of FIG. 5A with that of FIG. 4A, it is noted that in FIG. 4A, the curve at the bottom right-hand side defines a deviation from the expected sine-wave trajectory, which is not present in that of FIG. 5A. In contrasting FIGS. 4B and 5B, it will be noted that in FIG. 4B, a portion of what should be a straight line is distorted. However, as illustrated in FIG. 5B, the present invention yields the expected straight line. The gaps illustrated in the images of each of FIGS. 4A, 4B, 5A and 5B are anticipated due to known detector gaps in the imaging device.

Table I illustrates full-width half-maximum (FWHM) resolution results for a set of four (4) data acquisitions with a point source at various FOV positions. Four separate 20 minute list-mode acquisitions of 64-bit detector-pair packets were performed. Each file contains approximately 7 M event packets. These list-mode files were each applied to a rebinning algorithm 100% compatible with the hardware architecture of the present invention. For each input file, an output file with 32-bit bin-address packets is generated. The 3-D image reconstruction was done using Unweighted-OSEM-3D (2 iterations, 16 subsets) but with no crystal-efficiency normalization applied. [6] The resulting image size is 256×256×207 voxels.

TABLE I

PRELIMINARY "UNNORMALIZED, SPAN 3" 3-D IMAGE RESOLUTION

| "Point Source Position" Voxel Centroid | X FWHM Resolution cm | Y FWHM Resolution cm | Z FWHM Resolution cm |
|---|---|---|---|
| "Center of FOV" x: 128, y: 141, z: 101 | 0.263 | 0.248 | 0.219 |
| "Plus 10 cm X" x: 205, y: 131, z: 109 | 0.249 | 0.296 | 0.233 |
| "Minus 10 cm X" x: 47, y: 141, z: 99 | 0.278 | 0.276 | 0.270 |
| "Minus 10 cm Y" x: 130, y: 54, z: 85 | 0.232 | 0.284 | 0.268 |

For this preliminary "Span 3" case and without proper normalization, FWHM image resolution appears good and fairly uniform across a 20 cm diameter within the FOV. While a span of 3 has been described, it will be understood by those skilled in the art that greater spans are also supported by the present invention. The device of the present invention further provides the capability of transmission event processing and the generation of planned "single-crystal-index coincidence-delayed" event packets needed for random variance reduction.

From the foregoing description, it will be recognized by those skilled in the art that a PETLINK™ DMA Rebinner (PDR) for improved LOR rebinning has been described. The PDR of the present invention includes a peripheral component interconnect (PCI) card for on-line translation of detector-pair event packets into bin-address packets. The PDR of the present invention delivers accurate axial and transaxial LOR nearest-neighbor rebinning and enables the more oblique LOR to be mapped into the proper sinogram bins, which provides for more optimal image resolution.

While the present invention has been illustrated by description of several embodiments and while the illustrative embodiments have been described in considerable detail, it is not the intention of the applicant to restrict or in any way limit the scope of the appended claims to such detail. Additional advantages and modifications will readily appear to those skilled in the art. The invention in its broader aspects is therefore not limited to the specific details, representative apparatus and methods, and illustrative examples shown and described. Accordingly, departures may be made from such details without departing from the spirit or scope of applicant's general inventive concept.

Having thus described the aforementioned invention, we claim:

1. A rebinner for nearest-neighbor rebinning in Positron Emission Tomography (PET) using on-line 3D axial LOR-to-bin mapping, said rebinner comprising:
    an interface card adapted to interface to data acquisition architecture associated with an imaging device, the data acquisition architecture including at least a processor, random access memory (RAM), an operating system, and a data storage device;
    at least one input device for communicating data from the imaging device to said interface card; wherein said interface card includes:
    at least one field programmable gate array (FPGA); and
    at least one memory device, coupled to said FPGA, for storing at least one look-up table (LUT);
    said interface card being provided for converting detector-pair event packets received from the imaging device via said input device into bin-address packets.

2. The rebinner of claim 1 wherein said interface card is a peripheral component interconnect (PCI) card.

3. The rebinner of claim 1, further comprising a second FPGA in communication with said at least one FPGA via a high-bandwidth (HBW) connection.

4. The rebinner of claim 1 wherein said at least one memory device is a flash chip.

5. The rebinner of claim 1 wherein said at least one FPGA and said at least one memory device define a digital pipeline, said digital pipeline being provided for performing the steps of:
    (a) encoding for at least one of emission, depth of interaction, and transmission operation;
    (b) generating a transaxial sinogram index and at least one axial correction parameters from transaxial detector pair indexes;
    (c) generating an uncorrected plane index and a segment index with an encoded ring difference value from the axial detector-pair indexes;
    (d) generating a delta correction for both the plane and segment;
    (e) generating a corrected-for-true-axial-position plane index and a corrected-for-true-axial-position segment index;
    (f) calculating a sinogram number as an index into a 3-D array of sinograms; and
    (g) calculating a final bin-address value.

6. A rebinner for nearest-neighbor rebinning in Positron Emission Tomography (PET) using on-line 3D axial LOR-to-bin mapping, said rebinner comprising:
    a peripheral component interconnect (PCI) card adapted to interface with data acquisition architecture associated with an imaging device, the data acquisition architecture including at least a processor, random access memory (RAM), an operating system, and a data storage device;
    at least one input device for communicating data from the imaging device to said PCI card;
    a plurality of field programmable gate arrays (FPGAs), each of said plurality of FPGAs being in communication with a subsequent of said plurality of FPGAs via a high-bandwidth (HBW) connection;
    a plurality of flash memory chips for storing at least one look-up table (LUT);
    said plurality of FPGAs and said at least one memory device defining a digital pipeline, said digital pipeline being provided for performing the steps of:
    (a) encoding for at least one of emission, depth of interaction, and transmission operation;
    (b) generating a transaxial sinogram index and at least one axial correction parameters from transaxial detector pair indexes;
    (c) generating an uncorrected plane index and a segment index with an encoded ring difference value from the axial detector-pair indexes;
    (d) generating a delta correction for both the plane and segment;
    (e) generating a corrected-for-true-axial-position plane index and a corrected-for-true-axial-position segment index;
    (f) calculating a sinogram number as an index into a 3-D array of sinograms; and
    (g) calculating a final bin-address value;
    said PCI card being provided for converting detector-pair event packets received from the imaging device via said input device into bin-address packets.

7. A rebinner for nearest-neighbor rebinning in Positron Emission Tomography (PET) using on-line 3D axial LOR-to-bin mapping, said rebinner comprising:
    an interface card directly connectable to data acquisition architecture associated with an imaging device, said interface card including a data port for receiving image data from said imaging device, and a plurality of Field Programmable Gate Arrays (FPGAs) and flash memory chips configured in a digital pipeline configuration, for processing image data received at said data port and sending processed image data to said data acquisition architecture; and
    an input device connecting an output of said imaging device to said data port.

8. The rebinner of claim 7, wherein said input device comprises an optical fiber channel.

* * * * *